United States Patent [19]

Bowen et al.

[11] Patent Number: 5,086,138
[45] Date of Patent: Feb. 4, 1992

[54] POLYMERIZABLE COMPOSITION

[75] Inventors: Joanna Bowen, Bleadon Hill; Roderick J. W. Bowers, Kensal Rise; Malcolm D. Purbrick, Bushey; Hans M. Wagner, Stanmore, all of England

[73] Assignee: Eastman Kodak Company, Rochester, N.Y.

[21] Appl. No.: 571,618

[22] PCT Filed: Jan. 4, 1990

[86] PCT No.: PCT/GB90/00013
§ 371 Date: Sep. 4, 1990
§ 102(e) Date: Sep. 4, 1990

[87] PCT Pub. No.: WO90/07527
PCT Pub. Date: Jul. 12, 1990

[30] Foreign Application Priority Data

Jan. 6, 1989 [GB] United Kingdom ............... 8900250

[51] Int. Cl.$^5$ ............... C08F 220/22; C08F 222/38; C08F 220/10
[52] U.S. Cl. ............... 526/245; 526/303.1; 526/328
[58] Field of Search ............... 526/245

[56] References Cited

U.S. PATENT DOCUMENTS 4,433,111  2/1984  Tighe et al. ............... 525/326.2
5,008,358  4/1991  Anderson et al. ............... 526/292.3

OTHER PUBLICATIONS

Lu Chengxun and Feng Xinde and Wang Chongqing and Li Dechang, Journal of Polymer Science, Polymer Chemistry Edition 18, 2411-2422, 1980.

Primary Examiner—Joseph L. Schofer
Assistant Examiner—Wu C. Cheng
Attorney, Agent, or Firm—Doreen M. Wells

[57] ABSTRACT

A polymerizable composition comprises (a) an ethylenically unsaturated diluent monomer comprising an ethylenically unsaturated fluorine-containing monomer; (b) an ethylenically unsaturated monomer containing a reactive ester group capable of coupling with an amino group-containing compound by the formation of an amide link; and, (c) a polymerization initiator. A polymer produced from the composition is capable of immobilizing an amino group-containing compound e.g. a protein. Such polymers are suitable for use in a variety of biomedical applications.

4 Claims, No Drawings

POLYMERIZABLE COMPOSITION

The invention relates to a polymerisable composition and to a polymer produced therefrom. Polymers which are biocompatible and which may be employed in a variety of biomedical applications may be produced from the compositions of the invention.

More particularly, polymers are provided which are capable of immobilizing compounds containing amino groups. Such compounds include proteins and amino acids. Specific applications of the polymers of the invention include affinity chromatography wherein an amino group-containing ligand is attached to the polymer and peptide synthesis.

For example, the polymers of the invention could be used for the separation of a component of a body fluid e.g. blood using a bioaffinity separation procedure. This could be achieved by bringing the body fluid into contact with the polymer having an appropriate protein ligand attached to its surface.

Preferred polymer compositions of the invention are those from which hydrogels may be produced. A hydrogel is a polymeric material that imbibes a significant proportion of water within a three dimensional network without causing dissolution of the polymer.

Die Makromolekulare Chemie 177, 683-689 (1976) describes the synthesis of monomers containing a reactive ester group capable of coupling with an amine by the formation of an amide link. More particularly, it suggests that copolymers of succinimido esters of ω-methacryloylaminocarboxylic acid and methacrylamide may be used as carriers for enzymes and drugs.

U.S. Pat. No. 4,330,440 describes an activated polymer matrix for use in affinity chromatography. A macroporous polymer having surface hydroxyl groups e.g. hydroxyethyl methacrylate is treated with a carbonylating agent to provide active groups which are capable of immobilising compounds containing amino groups.

U.S. Pat. No. 4,433,111 describes polymeric materials suitable for biomedical applications, particularly for making contact lenses. The materials have enhanced surface properties which improve their protein repellency. Examples of other biomedical applications which are mentioned in the specification include surgical implants and prosthetic devices e.g. blood vessels, artificial urethers, heart valves and artificial breast tissue. The polymeric materials are also said to be useful for contact with body fluids outside the body e.g. in manufacturing membranes for kidney dialysis and heart/lung machines, swabs, nappy liners and wound dressings.

The hydrogel-forming polymeric material of U.S. Pat. No. 4,433,111 comprises units derived from (1) an olefinically unsaturated carboxylic acid amide, (2) an N-vinyl lactam, (3) an olefinically unsaturated carboxylic acid ester, (4) an olefinically unsaturated carboxylic acid and (5) a hydrophobic monomer comprising (a) a fluorine-containing polymerisable monomer having a fluoroaliphatic side chain and (b) a non-fluorine-containing polymerisable hydrophobic vinyl monomer. The various units are present in specified amounts and the copolymer is cross-linked with a cross-linking agent. The disclosure demonstrates the ability of the fluorine-containing monomer to affect the surface energy of the polymer and increase its protein repellency.

Unlike the polymer compositions of the present invention, the hydrogels according to U.S. Pat. No. 4,433,111 are specifically designed to be unreactive i.e. they do not contain reactive groups for the purpose of reacting with other compounds. While the polymer compositions of U.S. Pat. No. 4,330,440 do contain such reactive groups, the compositions and their preparation have a number of disadvantages. In this respect, the compositions require the provision of a macroporous polymer followed by separate steps to activate the polymer. Further, no action is taken to minimise non-specific adsorption to the polymer i.e. the adsorption of compounds other than those intended to react with the active groups. Similarly, the polymer compositions of Die Makromolekulare Chemie 177, 683-689 (1976) are reactive but make no provision for minimising non-specific adsorption.

The present invention aims to overcome disadvantages associated with prior art compositions by providing a polymerisable composition from which a desired activated polymer may be rapidly prepared. The method of preparation offers a high degree of control over the composition of the polymer and the monomers are chosen such that non-specific adsorption is reduced.

The invention provides a polymerisable composition comprising an ethylenically unsaturated diluent monomer comprising an ethylenically unsaturated fluorine-containing monomer;

an ethylenically unsaturated monomer containing a reactive ester group capable of coupling with an amino group-containing compound by the formation of an amide link; and, a polymerisation initiator.

The invention also provides a method of making a polymer having reactive ester groups which method comprises forming the polymerisable composition of the invention and subjecting the composition to conditions which generate free radicals from the polymerisation initiator.

Preferably, the diluent monomer is present in an amount from 65 to 99 mole percent and the monomer containing the reactive ester group is present in an amount from 1 to 35 mole percent, said percentages being based on the total monomer present.

The diluent monomer is chosen to provide the composition with desired physical properties. It is preferred that it comprises non-fluorine-containing monomer in addition to the fluorine-containing monomer. Any non-fluorine-containing monomer is preferably hydrophilic to minimise the non-specific adsorption of proteins to the polymer. Preferably, the diluent monomer or monomers are chosen to ensure that the polymerisable composition is coatable and film-forming either with or without the aid of a solvent. In a particularly preferred embodiment, the combination of monomers in the polymerisable composition form a solution without requiring a non-polymerisable solvent. An advantage of such a totally polymerisable composition is that it overcomes the problem of leaching out of small molecules, for example molecules associated with the initiation of polymerisation, which occurs with polymer membranes prepared by other methods. The concentration of the diluent monomer can be varied to adjust the level of reactive groups in the polymer to the desired range.

Preferred non-fluorine-containing diluent monomers are selected from esters of ethylenically unsaturated carboxylic acids (e.g. substituted or unsubstituted alkyl esters of acrylic or methacrylic acid), amides of ethylenically unsaturated carboxylic acids (e.g. N-alkyl substituted or unsubstituted amides of acrylic or methacrylic acid), N-vinyl substituted amides of carboxylic acids or N-vinyl substituted nitrogen-containing heterocyclic monomers. Examples of suitable diluent monomers include acrylamide, methacrylamide, N-substituted acrylamide and methacrylamide e.g. N-alkyl acrylamide and N,N-dialkyl acrylamide, alkyl acrylates and alkyl methacrylates wherein the alkyl groups are optionally substituted, N-vinyl-2-pyrrolidone and N-methyl-N-vinylacetamide.

For the formation of hydrogels, the diluent monomer is preferably a hydroxyalkyl acrylate, hydroxyalkyl methacrylate, glycidyl acrylate, glycidyl methacrylate, hydroxyalkylacrylamide or hydroxyalkylmethacrylamide monomer in which the alkyl group preferably contains from 1 to 6 carbon atoms.

Preferably, the fluorine-containing diluent monomer is a fluoroalkyl ester or amide of an ethylenically unsaturated carboxylic acid.

Examples of preferred ethylenically unsaturated fluorine-containing monomers include fluoroalkyl acrylates, fluoroalkyl methacrylates, fluoroalkylacrylamides and fluoroalkyl methacrylamides. The fluoroalkyl group may be partially or fully fluorinated and preferably contains from 1 to 6 carbon atoms. Particularly preferred fluoroalkyl groups terminate in a trifluoromethyl group and include trifluoroethyl.

All or part of the diluent monomer may be a fluorine-containing monomer. Preferably, the fluorine-containing monomer is present in an amount from 5 to 40 mole percent and the non-fluorine-containing monomer is present in an amount from 25 to 94 mole percent based on the total monomer present in the composition.

The monomer containing a reactive ester group capable of coupling with an amino group-containing compound, hereinafter also referred to as the reactive ester monomer, may be derived from an ester or amide of an ethylenically unsaturated carboxylic acid e.g. an acrylate, methacrylate, acrylamide or methacrylamide monomer.

Preferred reactive ester groups are represented by the formula —COOX wherein X represents an electron-withdrawing group. Functional groups are classified as electron-withdrawing groups relative to hydrogen, e.g. —$NO_2$ and —I groups draw electrons to themselves more than a hydrogen atom occupying the same position in the molecule. J. March, Advanced Organic Chemistry, 2nd edition, McGraw Hill, p 20,246. Specific examples of X groups include N-succinimido, benzylidene aniline, pentafluorophenyl, 4-nitrophenyl, 4-cyanophenyl, 4-alkylsulphonylphenyl, acyl, 4-acylphenyl, 4-dialkylaminocarbonylphenyl, 4-alkoxycarbonylphenyl and 4-alkoxysulphonylphenyl.

Preferably, a chain of from 4 to 15 atoms separates the reactive ester group from the ethylenically unsaturated portion of the monomer which undergoes polymerisation. Such a chain may comprise an alkylene chain. The purpose of the chain is to ensure that the reactive ester group is spaced away from the polymer backbone after polymerisation.

The reactive ester group reacts directly with the amino group-containing compound. Preferably, such reaction will take place under physiological reaction conditions.

Preferred polymerisable compositions may comprise from 5 to 25 mole percent reactive ester monomer and from 75 to 95 mole percent diluent monomer.

The polymerisation initiator is a compound or a combination of compounds which is capable of generating the free radicals required for polymerisation to occur. A wide variety of polymerisation initiators are known including thermal and photoinitiators. Such initiators include carbonyl compounds, organic sulphur compounds, peroxides, redox systems, azo and diazo compounds and halogen compounds.

The composition of the invention preferably comprises a photopolymerisation initiator. A particularly preferred photopolymerisation initiator is a combination of an aromatic carbonyl compound and an amine compound. Advantages associated with the use of such an initiator system are that polymerisation proceeds rapidly and can be carried out at room temperature.

Particularly preferred aromatic carbonyl compounds include ketocoumarin compounds. Specific examples of preferred aromatic carbonyl compounds include 2,2'-dimethoxy-2-phenylacetophenone, 3,3'-carbonyl-bis-(5,7-di-n-propoxycoumarin), 3,3'-carbonyl-bis-(7-diethylaminocoumarin) and 7-diethylamino-3-thenoylcoumarin.

A preferred example of an amine coinitiator compound is N-phenylglycine.

In addition to the components described above, the polymer composition of the invention may comprise a crosslinking agent. Many suitable crosslinking agents are known and include alkylene glycol diacrylates and dimethacrylates e.g. ethylene glycol dimethacrylate, and other polyfunctional compounds such as N,N'-methylene-bis-acrylamide and divinylbenzene.

The monomers used in the invention may be readily prepared and some are commercially available.

The fluorine-containing monomers and the monomers containing a reactive ester group used in the invention may be prepared by appropriate modifications of established literature techniques e.g. H. -G Batz, J. Koldehoff; Makromol. Chem. 177, 683 (1976) and W de Winter, A. Marien; Makromol. Chem., Rapid Commun. 5, 593 (1984).

In order to produce the reactive ester-containing monomer, the basic monomer e.g. acrylamide may be converted into a carboxy terminated derivative e.g. acrylamidocaproic acid which in turn may be esterified to provide a terminal reactive ester group e.g. a succinimido ester. A representative preparative method is given in Die Makromolekulare Chemie 177, 683–689 (1976).

The polymerisable composition of the invention may be prepared by mixing the individual components using a solvent if required. By the appropriate choice of monomers, no solvent is necessary. For example, all the monomers may be liquids or the diluent monomer can act as a solvent for the other monomers present.

By way of example, the polymerisable composition of the invention may be prepared by dissolving the fluorine-containing monomer, the reactive ester monomer and, optionally, a cross-linking agent in a solvent monomer. Subsequently, the polymerisation initiator e.g. a combination of ketocoumarin and amine compounds dissolved in solvent monomer, may be added to and mixed with the polymer composition.

A reactive ester-containing polymer is produced as a result of polymerising the polymerisable composition of the invention under conditions which generate free radicals from the polymerisation initiator e.g. using heat and/or radiation when required.

For example, using a thermal initiator the polymerisable composition may be heated to a temperature from 50° to 80° C. and polymerisation allowed to proceed for from 0.5 to 30 hours. Using a photoinitiator, polymerisation may be carried out at ambient temperature for from 0.5 to 4 hours.

The invention includes xerogels and hydrogels derived from the polymerisable composition of the invention.

The polymers of the invention may be used in a variety of forms.

The polymerisable composition may be formed into a shaped polymeric article by introducing the composition into a mould of the desired configuration before polymerisation is effected.

For example, a xerogel membrane may be prepared by injecting the polymer composition into a polymerisation cell formed by two glass plates which are clamped together and separated by a gasket. Preferably, the surfaces of the mould in contact with the polymerisable composition are treated with a mould release agent. Examples of suitable mould release agents include silicones and fluorocarbon compounds. Polymerisation e.g. by exposure to UV light, results in the formation of a xerogel membrane.

The shaped article may be immersed in water or an aqueous medium until equilibrium is reached. The water content of the hydrogel so produced will depend on the nature of the copolymer and its structure.

Alternatively, the polymerisable composition may be coated as a layer on a support.

An amino group containing-compound may be coupled to the polymer by contacting the polymer with the compound. The compound may be a ligand capable of interacting selectively with another compound whereby the polymer may be used for affinity chromatography. Examples of amino group-containing ligands include proteins.

The invention is further illustrated by way of example as follows. (The molar ratio of monomer components is given in parenthesis after each polymer).

EXAMPLE 1

Synthesis of
poly(acrylamide-co-N-(2,2,2-trifluoroethyl)methacrylamide-co-N-methacryloylaminocaproic acid, succinimido ester) (7:3:1)

The following was placed in a round-bottomed flask, fitted with a reflux condenser, stirrer and nitrogen inlet:

| | |
|---|---|
| acrylamide | 4.97 g |
| 2,2,2-trifluoroethylmethacrylamide | 5.01 g |
| methacrylamidocaproic acid, N-hydroxysuccinimido ester | 2.96 g |
| azobisisobutyronitrile | 0.06 g |
| dimethylformamide | 30 ml |

The reaction mixture was stirred for 5 hours at 60° C. under a nitrogen blanket. At the end of this period, the viscous solution was diluted with dimethylformamide (30 ml) and, after standing overnight, the polymer was precipitated into diethyl ether. The polymer was washed with acetone.

Yield: 10.3 g.

Analysis: Theory C 49.15, H 6.11, F 13.21, N 12.98, O 18.55%. Found C 47.52, H 6.53, F 12.84, N 11.92, O 21.19%.

Using the synthesis procedure described above, the following polymers were prepared:

poly(acrylamide-co-N-(2,2,2-trifluoroethyl)-methacrylamide-N-methacryloylaminocaproic acid, succinimido ester) (10:1:1, 8:2:1, 6:4:1, 5:5:2)

poly(acrylamide-co-N-(2,2,2-trifluoroethyl)-methacrylamide-co-N-methacryloyl-beta-alanine, succinimido ester) (8:2:1)

poly(acrylamide-co-N-(2,2,2-trifluoroethyl)methacrylamide-co-N-methacryloylaminocaproic acid, p-nitrophenyl ester) (16:4:1)

poly(acrylamide-co-N-(2,2,2-trifluoroethyl)-methacrylamide-co-N-methacryloylglyclglycine, succinimido ester) (8:1:2, 8:2:1)

poly(acrylamide-co-N-(2,2,2-trifluoroethyl)methacrylamide-co-N-methacryloyl-omega-aminoundecanoic acid, succinimido ester) 8:2:1)

poly(2-hydroxyethyl methacrylate-co-2,2,2-trifluoroethyl methacrylate-co-N-methacryloylaminocaproic acid, succinimido ester) (18:1:1)

poly(2-hydroxypropylmethacrylamide-co-N-(2,2,2-trifluoroethyl)methacrylamide-co-N-methacryloylaminocaproic acid, pentafluorophenyl ester) (8:2:1)

poly(2-hydroxypropyl methacrylate-co-2,2,2-trifluoroethyl methacrylate-co-N-methacryloylaminocaproic acid, succinimido ester) (8:1:2, 8:2:1)

poly(2-hydroxypropyl methacrylate-co-2,2,2, -trifluoroethyl methacrylate-co-N-methacryloylglycylglycine, p-nitrophenyl ester) (8:2:1)

poly(2-hydroxypropyl methacrylate-co-2,2,2-trifluoroethyl methacrylate-co-N-methacryloylglycylglycine, succinimido ester) (8:2:1)

poly(N-methyl-N-vinylacetamide-co-N-(2,2,2-trifluoroethyl)methacrylamide-co-N-methacryloylaminocaproic acid, succinimido ester) (8:2:1)

poly(N,N-dimethylacrylamide-co-N-(2,2,2-trifluoroethyl)methacrylamide-co-N-methacryloyl-beta-alanine, succinimido ester) (8:2:1)

poly(N,N-dimethylacrylamide-N-(2,2,2-trifluoroethyl)-methacrylamide-co-N-methacryloylaminocaproic acid, succinimido ester) (8:2:1)

poly(2-hydroxypropylmethacrylamide-co-N-(2,2,2-trifluoroethyl)methacrylamide-co-N-methacryloylaminocaproic acid, p-nitrophenyl ester-co-N-methacryloyl-omega-aminoundecanoic acid, p-nitrophenyl ester) (16:4:1:1, 8:2:1:1)

poly(N-(2,2,2-trifluoroethyl)methacrylamide-co-N-methacryloylaminocaproic acid, succinimido ester) (5:1)

poly(N-(2,2,2-trifluoroethyl)methacrylamide-co-N-methacryloylaminocaproic acid, p-nitrophenyl ester) (10:1)

A coating solution was prepared by dissolving poly(acrylamide-co-N-(2,2,2-trifluoroethyl)methacrylamide-co-N-methacryloylaminocaproic acid, succinimido ester) (7:3:1) (10% w/w) in dimethylformamide. The coating solution also contained glutaraldehyde (10% w/w based on the polymer) as a crosslinking agent.

The solution was coated on a polyester (ESTAR) sheet using a gravure roller at a coating speed of 1 to 2 m/min to provide a wet laydown of 2.5 mls per 250 cm$^2$.

A sample of the dried, crosslinked coated product was treated with a solution of albumin (an amino group-containing protein). Infra-red spectral analysis of the treated and untreated coating confirmed that the protein had coupled to the polymer at the active ester sites in the polymer as a result of amide formation.

EXAMPLE 2

Preparation of poly(2-hydroxypropyl methacrylate-co-epsilon methacrylamidocaproic acid succinimido ester (MCS)-2,2,2-trifluoroethylmethacrylamide (TFEMA)

MCS (13.5 mmoles, 4.0 g), TFEMA (12.0 mmoles, 2.0 g) and the bifunctional crosslinking agent, ethylene glycol dimethacrylate (EGDMA) (1.68 mmoles, 0.34 g) were dissolved in 2-hydroxypropyl methacrylate (103.6 mmoles, 14.0 mls), immersing the mixture in an ultrasonic bath to hasten dissolution. 7.9 mls of the following initiator stock solution was added:

| 3,3'-carbonyl-bis-(5,7-di-N-propoxycoumarin) | (0.55 mmoles) 0.30 g |
| --- | --- |
| N-phenylglycine (NPG) | (4.63 mmoles) 0.70 g |
| 2-hydroxypropyl methacrylate | 50 ml |

Mixing was effected through brief re-immersion in the ultrasonic bath, and three identical polymerisation cells were completely filled with the resultant solution.

The photopolymerisation cells were constructed from two glass plates, separated by a poly(tetrafluoroethylene) gasket. Prior to positioning of the gasket, the internal glass faces of the cell were covered with a mould release agent. The appropriate volumes of monomer, attendant photoinitiator and cross-linking agent were injected into the cell, held together with spring release clips, with a glass syringe and needle pre-positioned within the cell.

The cells were placed on the plate glass diffuser of an exposure frame, where they were exposed to an array of four 125 watt medium pressure vapour UV lamps for a period of 1.5 hours.

After exposure, photopolymerised xerogels were removed from the cell by release of the clips and separation of the glass plates. Surface characterisation of the xerogels was performed by electron spectroscopy.

The xerogel membranes were transparent indicating that the homogeneity of the polymers was good.

The polymer membranes produced in this manner were readily hydrated to form hydrogels.

We claim:

1. A polymerisable composition comprising an ethylenically unsaturated diluent monomer comprising at least 5 mole percent of an ethylenically unsaturated fluorine-containing monomer based on total monomer;

an ethylenically unsaturated monomer containing a reactive ester group capable of coupling directly with an amino group-containing compound by the formation of an amide link wherein the reactive ester group has the formula —COOX wherein X represents an electron withdrawing group; and, 2. A composition according to claim 1 wherein the diluent monomer is present in an amount from 65 to 99 mole percent and the monomer containing the reactive ester group is present in an amount from 1 to 35 mole percent.

3. A composition according to claim 1 or claim 2 wherein the diluent monomer further comprises a non-fluorine-containing monomer which is an ester or amide of an ethylenically unsaturated carboxylic acid, an N-vinyl substituted amide of a carboxylic acid or an N-vinyl substituted nitrogen-containing heterocyclic monomer.

4. A composition according to claim 3 wherein the non-fluorine-containing monomer is a hydroxyalkyl acrylate, hydroxyalkyl methacrylate, glycidyl acrylate, glycidyl methacrylate, hydroxyalkylacrylamide or hydroxyalkylmethacrylamide monomer.

* * * * *

UNITED STATES PATENT AND TRADEMARK OFFICE
CERTIFICATE OF CORRECTION

PATENT NO. : 5,086,138
DATED : February 4, 1992
INVENTOR(S) : Joanna Bowen, et. al.

It is certified that error appears in the above-indentified patent and that said Letters Patent is hereby corrected as shown below:

Claim 1, Column 8, line 19 reads:

represents an electron withdrawing group; and

Claim 1, Column 8, line 19 should read:

represents an electron withdrawing group; and a polymerisation initiator.

Signed and Sealed this

Twenty-first Day of December, 1993

*Attest:*

BRUCE LEHMAN

*Attesting Officer*  *Commissioner of Patents and Trademarks*